United States Patent
Wu et al.

(10) Patent No.: US 7,756,239 B2
(45) Date of Patent: Jul. 13, 2010

(54) DIAGNOSTIC IMAGING TWO NON K-EDGE BASIS MATERIALS PLUS N K-EDGE CONTRAST AGENTS

(75) Inventors: Xiaoye Wu, Rexford, NY (US); Robert F. Senzig, Germantown, WI (US); Deborah Joy Walter, Terre Haute, IN (US); James W. LeBlanc, Niskayuna, NY (US); John Eric Tkaczyk, Delanson, NY (US)

(73) Assignee: General Electric Company, Schenectady, NY (US)

( * ) Notice: Subject to any disclaimer, the term of this patent is extended or adjusted under 35 U.S.C. 154(b) by 7 days.

(21) Appl. No.: 11/608,162

(22) Filed: Dec. 7, 2006

(65) Prior Publication Data

US 2008/0137803 A1 Jun. 12, 2008

(51) Int. Cl.
*A61B 6/00* (2006.01)
(52) U.S. Cl. .............................. 378/5; 378/4; 378/98.9; 378/98.11
(58) Field of Classification Search ..................... 378/4, 378/156, 207, 901, 98.9, 98.11, 98.12
See application file for complete search history.

(56) References Cited

U.S. PATENT DOCUMENTS

| 3,848,130 | A | * | 11/1974 | Macovski | ................ | 378/98.9 |
| 3,974,386 | A | * | 8/1976 | Mistretta et al. | ......... | 378/98.11 |
| 4,029,963 | A | * | 6/1977 | Alvarez et al. | ................ | 378/5 |
| 4,686,695 | A | * | 8/1987 | Macovski | ................ | 378/146 |
| 4,963,746 | A | * | 10/1990 | Morgan et al. | ......... | 250/363.02 |
| 5,115,394 | A | * | 5/1992 | Walters | ................ | 382/131 |
| 5,953,444 | A | * | 9/1999 | Joseph et al. | ................ | 382/131 |
| 6,614,878 | B2 | * | 9/2003 | Bogatu et al. | ................ | 378/158 |
| 6,813,333 | B2 | * | 11/2004 | Karau et al. | ................ | 378/4 |
| 6,891,918 | B2 | | 5/2005 | Drummond et al. | | |
| 7,236,559 | B2 | * | 6/2007 | Jha et al. | ................ | 378/5 |
| 2004/0101089 | A1 | * | 5/2004 | Karau et al. | ................ | 378/4 |
| 2004/0184574 | A1 | * | 9/2004 | Wu et al. | ................ | 378/5 |
| 2004/0264627 | A1 | * | 12/2004 | Besson | ................ | 378/5 |

(Continued)

OTHER PUBLICATIONS

Thompson et al., X-ray Data Booklet Center for X-ray Optics and Advanced Light Source, Lawrence Berkeley National Laboratory, 2005, Section 1.1-1.6.*

(Continued)

*Primary Examiner*—Edward J Glick
*Assistant Examiner*—Alexander H Taningco
(74) *Attorney, Agent, or Firm*—Ziolkowski Patent Solutions Group, SC

(57) ABSTRACT

A diagnostic imaging system in an example comprises a high frequency electromagnetic energy source, a detector, a data acquisition system (DAS), and a computer. The high frequency electromagnetic energy source emits a beam of high frequency electromagnetic energy toward an object to be imaged and be resolved by the system. The detector receives high frequency electromagnetic energy emitted by the high frequency electromagnetic energy source. The DAS is operably connected to the detector. The computer is operably connected to the DAS and programmed to employ an inversion table or function to convert N+2 measured projections at different incident spectra into material specific integrals for N+2 materials that comprise two non K-edge basis materials and N K-edge contrast agents. N comprises an integer greater than or equal to 1.

19 Claims, 6 Drawing Sheets

U.S. PATENT DOCUMENTS

| | | | |
|---|---|---|---|
| 2005/0084060 A1* | 4/2005 | Seppi et al. ..................... | 378/5 |
| 2005/0084069 A1* | 4/2005 | Du et al. ..................... | 378/98.9 |
| 2005/0123093 A1* | 6/2005 | Lawaczeck et al. ...... | 378/98.11 |
| 2005/0259781 A1* | 11/2005 | Ying et al. ..................... | 378/5 |
| 2006/0067473 A1* | 3/2006 | Eberhard et al. ........... | 378/98.9 |
| 2007/0167716 A1* | 7/2007 | Kinahan et al. ............. | 600/407 |

OTHER PUBLICATIONS

Coronary Angiography, http://detserv1.dl.ac.uk/herald/xray_review_angiography.htm.

Dual Energy K-Edge Subtraction (KES), http://www.lightsource.ca/bioimaging/k-edge.htm.

High-Z Limiter Materials, http://www.fz-juelich.de/ipp/highz/.

Definition of "K edge" from Medcyclopaedia, http://www.medcyclopaedia.com/library/topics/volume_i/k/k_edge.aspx?p=1.

The Laue Method and Synchrotron Radiation, http://www.aip.org/pt/vol-54/iss-7/captions/p33box1.html.

Definition of "Photoelectric Absorption" from Medcyclopaedia, http://www.medcyclopaedia.com/library/topics/volume_i/p/photoelectric_absorption/dphotoelectric_absorpt_fig1.aspx.

Cheng et al., "Transmission and Dose Perturbations with High-Z Materials in Clinical Electron Beams".

* cited by examiner

DIAGNOSTIC IMAGING TWO NON K-EDGE BASIS MATERIALS PLUS N K-EDGE CONTRAST AGENTS

BACKGROUND OF THE INVENTION

The present invention relates generally to diagnostic imaging and, more particularly, to a method and apparatus of detecting materials with K-edge absorption in an effective energy region covered by an incident x-ray spectrum.

Exemplary diagnostics devices comprise x-ray systems, magnetic resonance (MR) systems, ultrasound systems, computed tomography (CT) systems, positron emission tomography (PET) systems, and other types of imaging systems. Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

An exemplary CT imaging system comprises an energy discriminating (ED) and/or multi energy (ME) CT imaging system that may be referred to as an EDCT and/or MECT imaging system. The EDCT and/or MECT imaging system in an example is configured to be responsive to different x-ray spectra. For example, a conventional third generation CT system acquires projections sequentially at different x-ray tube potentials. Two scans in an example are acquired either back to back or interleaved in which the tube operates at 80 kVp and 160 kVp potentials. Special filters in an example are placed between the x-ray source and the detector such that different detector rows collect projections of different x-ray energy spectra. The special filters that shape the x-ray spectrum in an example can be used for two scans that are acquired either back to back or interleaved. Energy sensitive detectors in an example are used such that each x-ray photon reaching the detector is recorded with its photon energy.

Exemplary ways to obtain the measurements comprise: (1) scan with two distinctive energy spectra, (2) detect photon energy according to energy deposition in the detector, and (3) photon counting. EDCT/MECT provides energy discrimination and material characterization. For example, in the absence of object scatter, the system derives the behavior at any other energy based on the signal from two regions of photon energy in the spectrum: the low-energy and the high-energy portions of the incident x-ray spectrum. In an exemplary energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two materials.

The conventional basis material decomposition (BMD) algorithm is based on the concept that in the energy region for medical CT, the x-ray attenuation of any given material can be represented by a proper density mix of two other materials, referred to as the basis materials. Based on the projections acquired at the two incident x-ray spectra, the BMD algorithm computes two sets of new projections, corresponding to two new CT images that each represents the equivalent density of one of the basis materials. Since a material density is independent of x-ray photon energy, these images are approximately free of beam-hardening artifacts. An operator can choose the basis material to target a certain material of interest, for example, to enhance the image contrast.

Medical CT images can be enhanced in certain applications by use of contrast agents. A contrast agent is injected and images can be taken below and above the K-edge absorption energy of the contrast agent to further the contrast agent. For example, the two images are logarithmically subtracted and show the details of the structure of those volumes containing the contrast agent.

A K-edge indicates a sudden increase in the attenuation coefficient of photons occurring at a photon energy just above the binding energy of the K shell electron of the atoms interacting with the photons. The sudden increase in attenuation is due to photoelectric absorption of the photons. For this interaction to occur, the photons have more energy than the binding energy of the K shell electrons. A photon having an energy just above the binding energy of the electron is therefore more likely to be absorbed than a photon having an energy just below this binding energy. A general term for the phenomenon is absorption edge.

Systems with K-edge contrast materials and/or agents do not fit into the conventional BMD model. The conventional BMD is directed to non K-edge materials. In addition, the conventional BMD cannot account for the K-edge effect of high Z or high atomic number materials such as iodine (I), barium (Ba), tungsten (W), gadolinium (Gd), and xenon (Xe) if the K-edge of the material lies in the active energy region of the incident x-ray spectrum. A design for resolving K-edge contrast agents has employed monochromatic x-ray beams with which the K-edge material can be resolved by imaging the object at photon energies slightly below and slightly above the K-edge, but prevents integration of monochromatic sources with sufficient x-ray flux into a rotating gantry and so limits the application from use as a practical monochromatic x-ray source in medical CT scanners. An exemplary K-edge material comprises a K-edge within an x-ray spectrum employed for a given, selected, and/or particular application. An exemplary non K-edge material may comprise no K-edge, or may comprise a K-edge that is outside the x-ray spectrum for such an application. For example, iodine comprises a K-edge at approximately 33.2 keV. Iodine does comprise a K-edge material in an exemplary low kVp system where the x-ray spectrum covers approximately 20 keV to approximately 50 keV. In another example, iodine would not be considered a K-edge material in a system where the x-ray spectrum starts from approximately 40 keV.

Developments in biotechnology show promise for contrast agents that target specific organs and/or diseases. These contrast agents can be designed to have high-Z elements with a K-edge above 50 keV. With this K-edge in the middle of the x-ray energy spectrum, the conventional BMD cannot account for discontinuity in the attenuation and fails to provide accurate results. Therefore, it would be desirable to design an apparatus and method to reduce a number of scans needed in diagnostic imaging to accurately detect a density of one or more K-edge contrast agents.

BRIEF DESCRIPTION OF THE INVENTION

The invention in an implementation encompasses a diagnostic imaging system. The diagnostic imaging system comprises a high frequency electromagnetic energy source, a detector, a data acquisition system (DAS), and a computer. The high frequency electromagnetic energy source emits a beam of high frequency electromagnetic energy toward an object to be imaged and be resolved by the system. The detector receives high frequency electromagnetic energy emitted by the high frequency electromagnetic energy source. The DAS is operably connected to the detector. The computer is operably connected to the DAS and programmed to employ an inversion table or function to convert N+2 measured projections at different incident spectra into material specific integrals for N+2 materials that comprise two non K-edge basis materials and N K-edge contrast agents. N comprises an integer greater than or equal to 1.

Another implementation of the invention encompasses a method. A diagnostic imaging system is calibrated through measurement of N+2 projections at different incident spectra of a substantially uniform mixture of a respective N+2 materials with known path integrated densities. The N+2 materials comprise two non K-edge basis materials and N K-edge contrast agents. N comprises an integer greater than or equal to 1.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Exemplary diagnostics devices comprise x-ray systems, magnetic resonance (MR) systems, ultrasound systems, computed tomography (CT) systems, positron emission tomography (PET) systems, and other types of imaging systems. Exemplary applications of x-ray sources comprise imaging, medical, security, and industrial inspection applications. The operating environment of an exemplary implementation comprises a 64-slice CT system. However, it will be appreciated by those skilled in the art that an exemplary implementation is applicable for use with single-slice or other multi-slice configurations. Moreover, an exemplary implementation is employable for the detection and conversion of x-rays. However, one skilled in the art will further appreciate that an exemplary implementation is employable for the detection and conversion of other high frequency electromagnetic energy and/or high frequency polychromatic electromagnetic energy. An exemplary implementation is employable with a "third generation" CT scanner and/or other CT systems.

Figure 1:
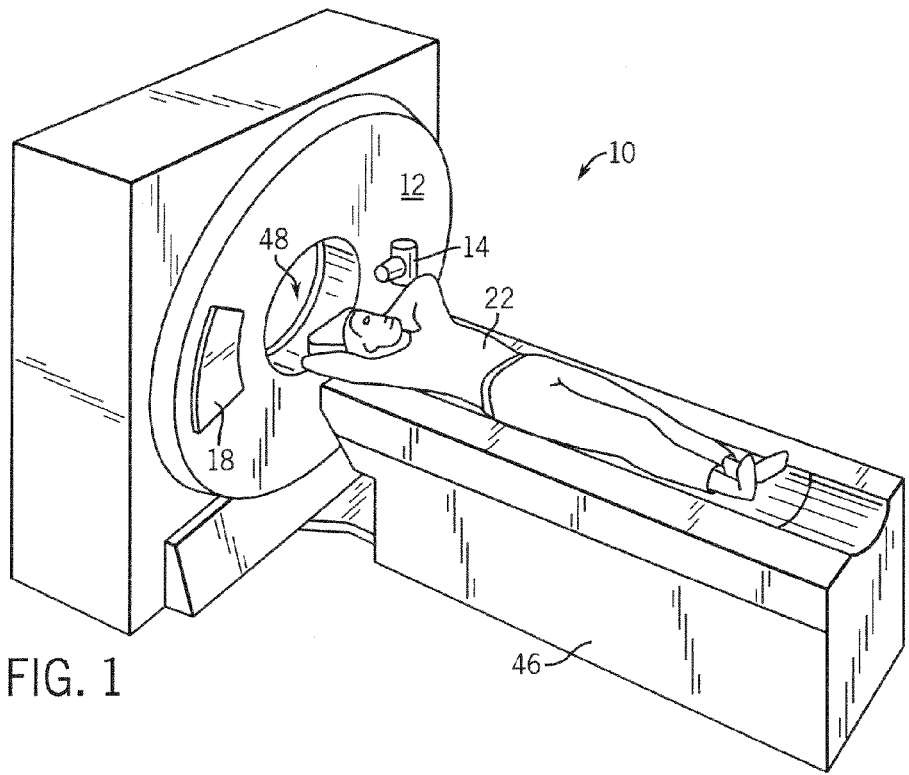
FIG. 1 is a pictorial view of an implementation of a CT imaging system.
Figure 2:
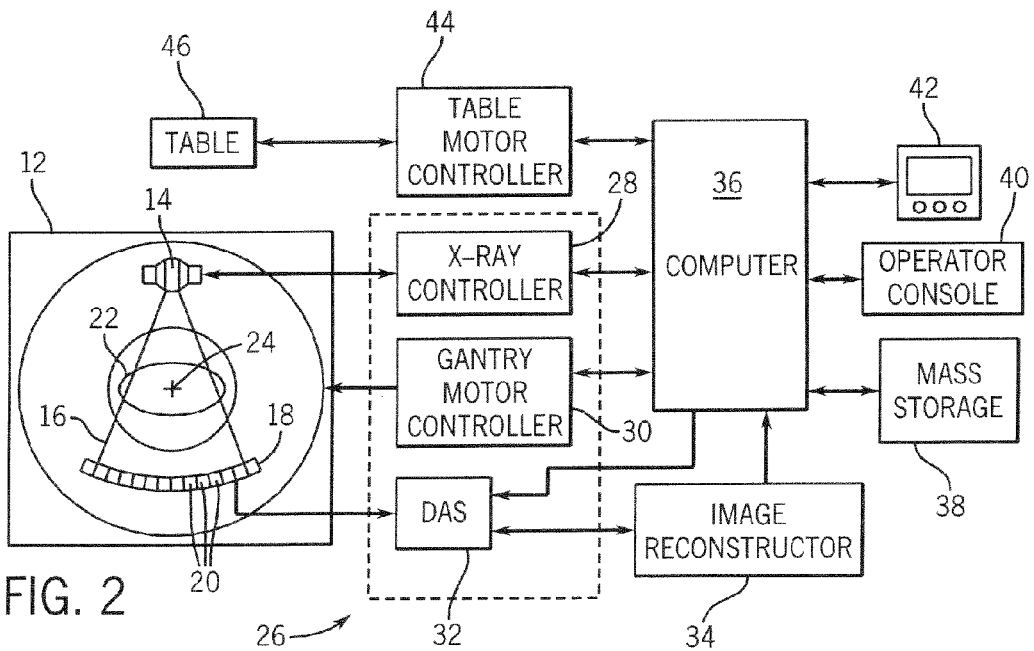
FIG. 2 is a block schematic diagram of an implementation of the system of FIG. 1.

Referring to FIGS. 1 and 2, a diagnostic and/or computed tomography (CT) imaging system 10 is shown as including a gantry 12 representative of a "third generation" CT scanner. The CT imaging system 10 in an example comprises an energy discriminating (ED) and/or multi energy (ME) CT imaging system that may be referred to as an EDCT and/or MECT imaging system. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. Exemplary detectors 20 comprise energy discriminating (ED) detectors. The ED detector as the detector 20 in an example obtains ED readout from the beam of x-rays 16. During a scan to acquire x-ray projection data, gantry 12 and the components mounted thereon rotate about a center of rotation 24, as will be appreciated by those skilled in the art.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

EDCT/MECT provides energy discrimination and material characterization. For example, in the absence of object scatter, the system derives the behavior at any other energy based on the signal from two regions of photon energy in the spectrum: the low-energy and the high-energy portions of the incident x-ray spectrum. In an exemplary energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object 22 composed of two materials.

A K-edge indicates a sudden increase in the attenuation coefficient of photons occurring at a photon energy just above the binding energy of the K shell electron of the atoms interacting with the photons. The sudden increase in attenuation is due to photoelectric absorption of the photons. For this interaction to occur, the photons have more energy than the binding energy of the K shell electrons. A photon having an energy just above the binding energy of the electron is therefore more likely to be absorbed than a photon having an energy just below this binding energy. Sudden increases in attenuation may also be found for inner shells other than the K shell. A general term for the phenomenon is absorption edge. An exemplary K-edge material comprises a K-edge within an x-ray spectrum employed for a given, selected, and/or particular application. An exemplary non K-edge material may comprise no K-edge, or may comprise a K-edge that is outside the x-ray spectrum for such an application. For example, iodine comprises a K-edge at approximately 33.2 keV. Iodine does comprise a K-edge material in an exemplary low kVp system where the x-ray spectrum covers approximately 20 keV to approximately 50 keV. In another example, iodine would not be considered a K-edge material in a system where the x-ray spectrum starts from approximately 40 keV.

Systems with K-edge materials and/or contrast agents do not fit into the conventional basis materials decomposition (BMD) model. In addition, the conventional BMD cannot account for the K-edge effect of high Z or high atomic number materials such as iodine (I), barium (Ba), tungsten (W), gadolinium (Gd), and xenon (Xe) if the K-edge of the material lies in the active energy region of the incident x-ray spectrum. An exemplary approach herein extends the BMD model to include any number of K-edge materials. An analytical approach herein obtains relatively and/or substantially accurate K-edge contrast agent densities.

An exemplary implementation may detect contrast agents with K-edge in the energy spectrum of an x-ray imaging system together with the detection of the non K-edge materials. An exemplary application of conventional BMD may be extended to a more and/or relatively complex object 22, for example, that comprises non K-edge materials and one or multiple K-edge materials and/or contrast agents. An exemplary implementation employs an exemplary ED detector as the detector 20 and exemplary placement of energy bins for the ED detector, for example, to analytically resolve the one or multiple K-edge materials and/or accurately measure their densities. The ED detectors as the detectors 20 in an example provide enhanced, desirable, optimal, and/or improved sensitivity in material decomposition. Another exemplary implementation employs detectors 20 other than instances of ED detectors and employs scans with multiple kVps, multiple distinct incident spectra using different kVps or beam filters.

An exemplary approach to material decomposition may apply analogously to one or more exemplary implementations that employ ED detectors as the detectors 20 and/or one or more exemplary implementations that employ multiple-kVp scans.

Presented herein is an exemplary approach to accurately detect the density of multiple K-edge contrast agents in a single CT scan, for example, using a conventional polychromatic x-ray source. An exemplary approach allows the use of multiple K-edge materials and/or contrast agents. Multiple K-edge materials in an example are resolved simultaneously in a single CT scan. This development in an example enhances the K-edge contrast agents with nearly one hundred percent specificity. Each of multiple K-edge contrast agents in an example is targeted to different tissues/organs in a single CT scan. Accurate densities of multiple K-edge contrast agents in an example are obtained analytically in a single CT scan. An exemplary implementation provides specificity of contrast agents. An exemplary approach recognizes that multiple non K-edge materials may result in the same and/or substantially the same BMD values as conventional BMD technique may obtain for materials identified through their components on the basis materials alone. This uncertainty is a physical phenomenon, regardless of the accuracy of the measurements. Each element does have a fixed and unique K-edge. So, an image of a given K-edge in an example may be directly associated to a given element with one hundred percent specificity or substantially one hundred percent specificity.

For example, an object 22 in an example may comprise three materials of different atomic number. Without exemplary K-edge imaging, bone may appear in BMD images with each of water and iodine as the basis. To x-rays in an exemplary energy range of interest for medical CT imaging such as 40 keV to 160 keV, the mixture of water and iodine absorbs x-ray photons the same way as the bone. The uncertainty of multiple candidate basis materials does not exist in exemplary K-edge imaging. For example, a detected K-edge at 50.23 keV corresponds to only gadolinium (Gd).

Figure 3:
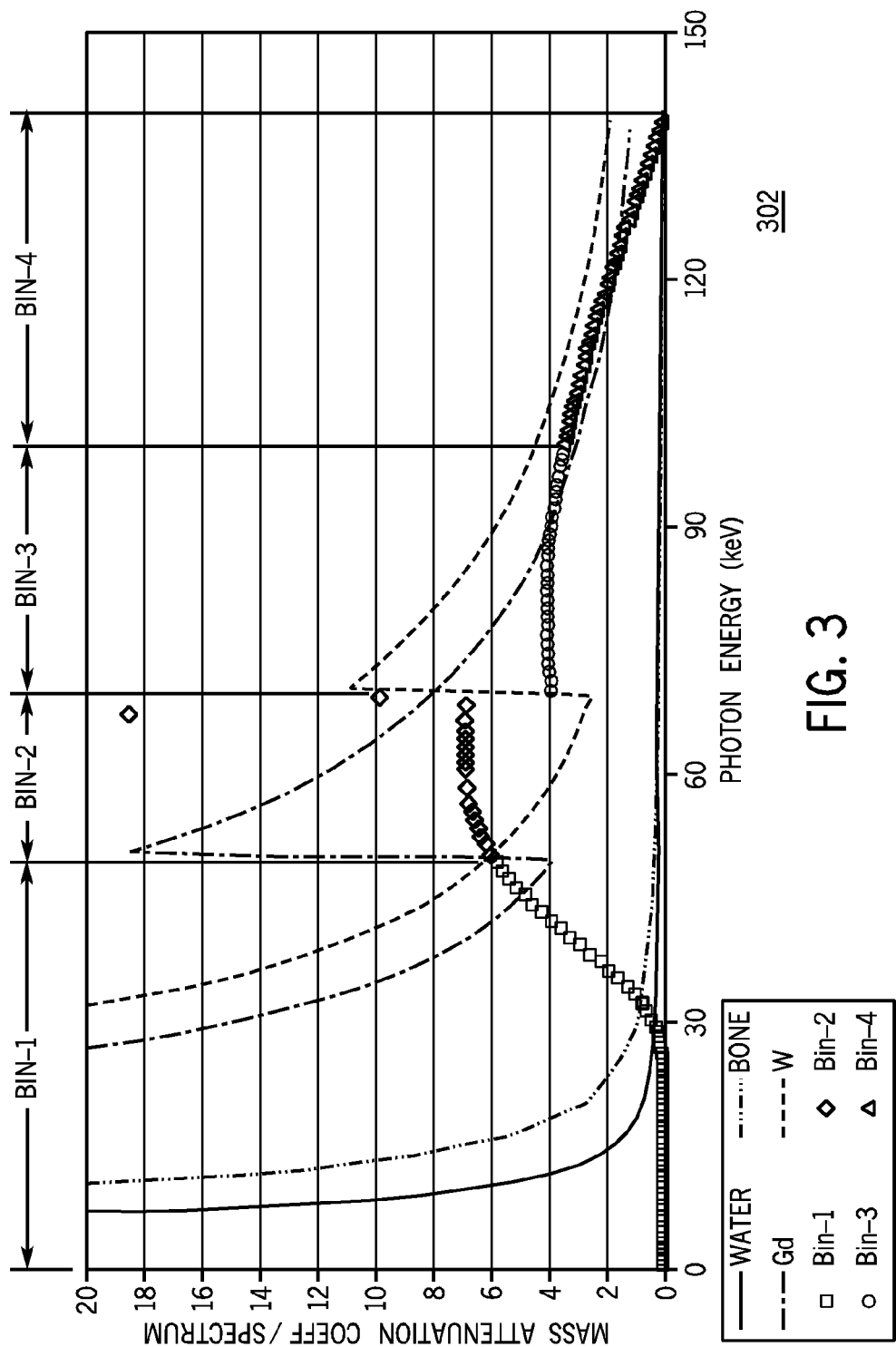
FIG. 3 is an exemplary plot of mass attenuation coefficient and spectrum versus photon energy through employment of a plurality of non K-edge materials and a plurality of K-edge materials and/or contrast agents by an implementation of the system of FIG. 1.

FIG. 3 is an exemplary plot 302 of mass attenuation coefficient and spectrum versus photon energy through employment of a plurality of non K-edge materials and a plurality of K-edge materials and/or contrast agents by the system 10. An exemplary system 10 employs four materials, for example, two non K-edge materials and two K-edge materials. Exemplary non K-edge basis materials comprise water and bone. The non K-edge and the K-edge materials in an example may be resolved effectively with four different kVp scans. In another example, the materials may be resolved with a four-energy bin ED system, for example, where the x-ray spectrum is divided into four energy bins and the integrated x-ray photon counts in each energy bin are separately recorded by the ED detectors as the detectors 20.

In an exemplary implementation, a multiple energy bin system using the ED detector as the detector 20 comprises enhanced, improved, and/or superior sensitivity. An exemplary approach chooses, selects, and/or determines the energy bins and the K-edge materials with exemplary roles such as one, multiple, and/or all of the following. All K-edges in an example are well within the x-ray spectrum. Certain separation of the K-edges in energy for different K-edge materials in an example is accepted, sought, and/or needed for desirable and/or good sensitivity, for example, 10 keV or more. Using the K-edge material for energy bin separation in an example enhances and/or improves sensitivity as represented in the plot 302, where the K-edge energies of both gadolinium (Gd) and tungsten (W) may be selected for the energy bin boundaries. An exemplary implementation comprises x-ray photon statistics in each of the energy bin that are well-balanced, for example, since image noise in an example may be dominated by substantially poor and/or very poor photon statistics in any of the energy bins. By tuning, selecting, and/or optimizing the energy bins for a given set of the K-edge materials, both the non K-edge materials and the K-edge materials in an example may be analytically resolved. Exemplary calibration of inversion matrix functions fm( ) lead to computation of the integrated density of the N+2 materials with the input data PPs, as described herein.

Figure 4:
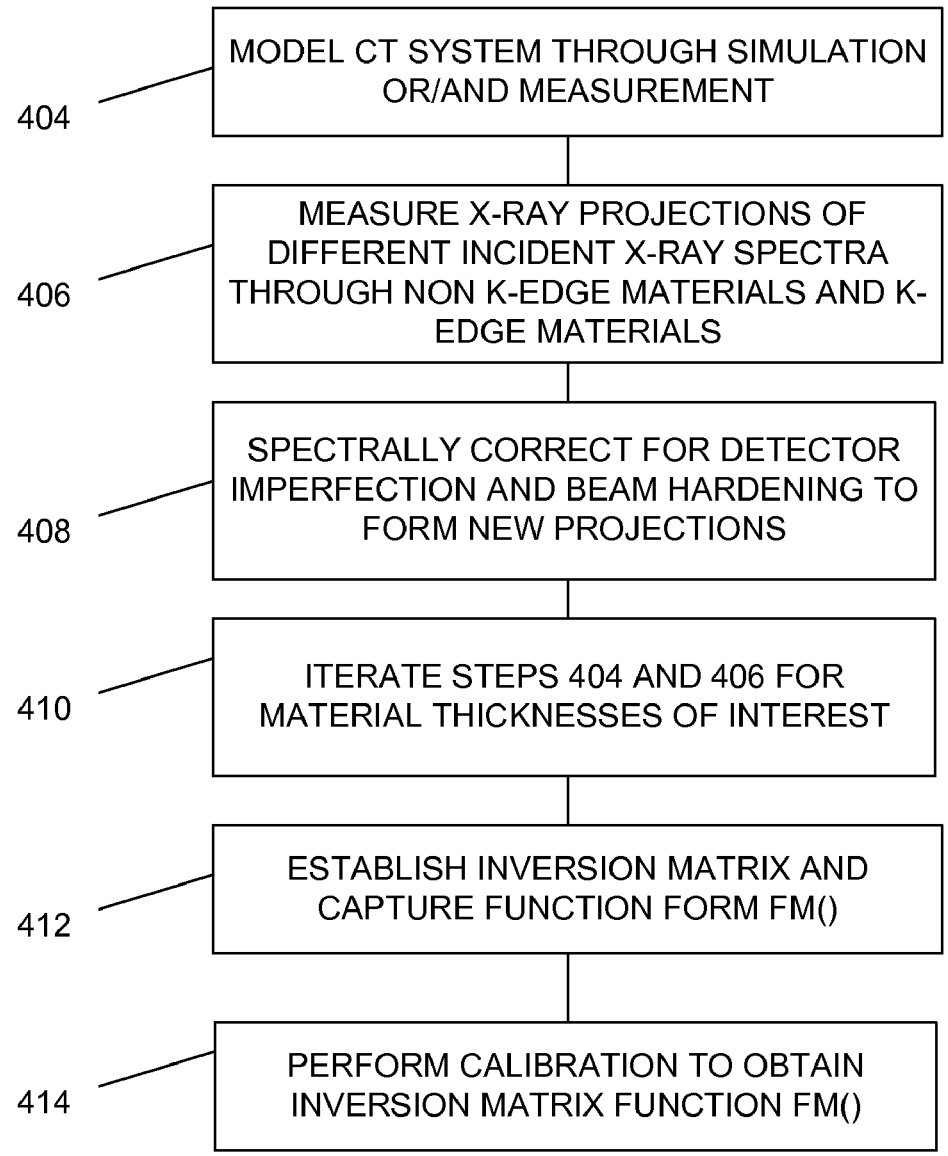
FIG. 4 is a representation of an exemplary logic flow for material decomposition that comprises employment of K-edge materials and/or contrast agents.

FIG. 4 is a representation of an exemplary logic flow 402 for material decomposition that comprises employment of K-edge contrast materials and/or agents. Calibration in an example serves to obtain an inversion matrix, for example, through employment of computer simulation and/or physical measurement at the scanner as the gantry 12 of the CT imaging system 10. Exemplary physical measurements involve material preparation and/or alignment. Exemplary simulation may incorporate various physical effects such as x-ray scatter and its associated correction algorithm into the computation of projection data set Ps in STEPS 406 and 408. Exemplary simulation may occur on a computer 36 connected within the system 10 and/or an instance of the computer 36 separate, isolated, decoupled, and/or disconnected from one or more additional components of the system 10. For example, a computer simulation may employ an additional instance of the computer 36 different from an instance of the computer 36 that later performs diagnostic imaging based on the computer simulation, as will be appreciated by those skilled in the art.

Figure 5:
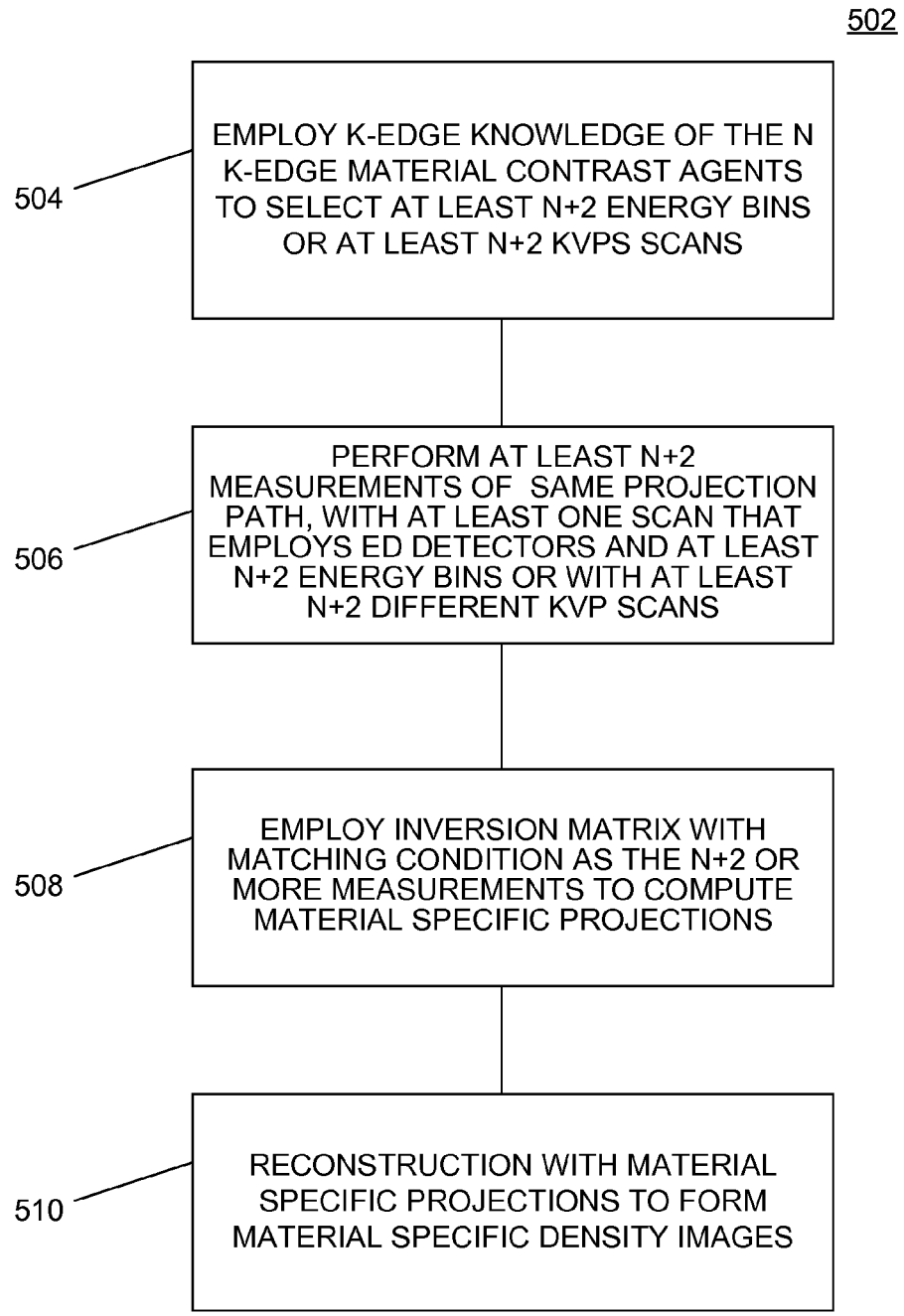
FIG. 5 is a representation of an exemplary logic flow for obtaining material specific projections and images.

N+2 measurements of the patient or object 22 in an example are performed. An exemplary employment of the inversion matrix, for example, with one or more functional forms fm( ) as described herein with reference to STEP 414 (FIG. 4), serves to obtain the material specific projections for image reconstruction. An exemplary and/or analogous approach is applicable to any N number of K-edge contrast materials and/or agents. Exemplary K-edge materials and/or contrast agents may comprise iodine (I), barium (Ba), tungsten (W), gadolinium (Gd), and xenon (Xe), for example, depending on the incident x-ray spectrum selected for an exemplary application. For a given combination of K-edge contrast materials and/or agents and x-ray beam spectrum, the logic flow 402 in an example need be performed only once. The computed functional form $f_m(\ )$ for each detector element/x-ray spectrum in an example may be stored for later use, for example, as described herein with reference to exemplary logic flow 502 (FIG. 5).

The logic flow 402 in an example is performed by a manufacturer or a qualified service person through employment of one or more components of the system 10. STEP 404 in an example prepares to model the CT system 10 through simulation or/and measurement. A targeted system in an example is modeled with two non K-edge basis materials plus the N K-edge contrast agents for a total of N+2 materials. For example, the object 22 may be modeled with two conventional non K-edge basis materials plus the N K-edge contrast agents for a total of N+2 materials to be employed for the material decomposition. STEP 406 in an example measures x-ray projections (p1, p2, ... ps) of N+2 different incident x-ray spectra through employment of two non K-edge materials and N K-edge materials of length (Lm1, Lm2, L1, L2, ... Lk), with unity density where s=N+2, and k=N. The two non K-edge materials in an example may be selected from among many choices, since these two materials in an example need not match the non K-edge materials employed in the objects and/or patients 22 that may be actually scanned. For example, any pair of non K-edge materials with distinctive x-ray mass attenuation coefficients in an example may serve to effectively model any non K-edge materials. STEPS 404 and 406 in an example obtain knowledge of an N number of K-edge contrast agents that will be injected into patient 22. STEP 408 in an example spectrally corrects for detector imperfection and beam hardening of (p1, p2, ... ps) of water to form new projections (P1, P2, ... Ps), for example, through employment of a medical CT scanner technique, as will be appreciated by those skilled in the art.

STEP 410 in an example iterates STEPS 404 and 406 for all and/or substantially all possible, desired, and/or selected material thicknesses (Lm1, Lm2, L1, L2, ... Lk), for example, of interest in imaging, for example, with resulting data pairs (Lm1, Lm2, L1, L2, ... Lk)→(P1, P2, ... Ps). For example, calibrations for all the possible K-edge contrast combinations may be performed before object or patient scan. STEP 412 in an example establishes an inversion matrix Lm=fm (P1, P2, ... Ps) and captures an associated function form $f_m(\ )$. The function form fm( ) in an example may be obtained with functional fitting to the measured data pairs from STEP 410 and/or through employment of a lookup table, where m=m1, m2, 1, ... N, for the exemplary two decomposition basis of the non K-edge materials and the N K-edge contrast materials. An exemplary implementation covers all the possible, desirable, expected, and/or planned K-edge materials in the N K-edge materials modeled. An exemplary calibration of the diagnostic imaging system 10 employs N+2 projections at the different incident spectra to cover a possible path integrated density range for all the N+2 materials in small incremental steps. For each data point in an example the integrated density of a given material is increased with a small amount compared to the entire range to be covered. Exemplary small incremental steps serve to evenly and/or substantially evenly divide the integrated density range such as an entirety of the range, for example, into twenty (20) to one hundred (100) points, parts, and/or incremental steps. An exemplary incremental size is a function of material. For example, an incremental size of 1.0 gram/cm$^2$ may be employed for water and 0.1 gram/cm$^2$ may be employed for iodine. An exemplary approach employs iteration to establish a large number and/or amount of data pairs. To capture the fm( ) function, an exemplary implementation of logic flow 402 employs all the data points.

An illustrative description of an exemplary computation of the inversion function fm( ) is presented, for explanatory purposes. Exemplary parameters such as in plot 302 may be defined for an exemplary system 10 with two K-edge materials.

1. $\mu(E), \mu1(E), \mu2(E), \mu gd(E)$ and $\mu w(E)$: the mass attenuation coefficients of any material, material-1, material-2, gadolinium, and tungsten, respectively, where E is the x-ray photon energy.
2. a1, a2, a3 and a4: the density of material-1, material-2, gadolinium and tungsten.
3. s1(E), s2(E), s3(E) and s4(E): the four distinct spectra, under which the projections are measured. These spectra may be from four kVps or the spectrum inside each of the four energy bins in plot 302.

As an exemplary extension to incorporate K-edge materials with two non K-edge material BMD, an exemplary general term to represent the x-ray mass attenuation coefficients of any material in an example may be expressed as exemplary equation (1), $$\mu(E) = a1\mu1(E) + a2\mu2(E) \quad \leftarrow \text{conventional } BMD \quad (1)$$
$$+ a3\mu gd(E) + a4\mu w(E) + \ldots \quad \leftarrow K\text{-edge}$$

By using exemplary equation (1), the measured projection data through different incident x-ray spectra in an example may be expressed by exemplary equations in (2), where the integration ∫dl is over the projection path.

$$p1 = -\log [\int s1(E)\exp(\int (a1(x,y)\mu1(E)+a2(x,y)\mu2(E)+a3(x,y)\mu gd(E)+a4(x,y)\mu w(E))dl)dE/(\int s1(E)de)]$$

$$p2 = -\log [\int s2(E)\exp(\int (a1(x,y)\mu1(E)+a2(x,y)\mu2(E)+a3(x,y)\mu gd(E)+a4(x,y)\mu w(E))dl)dE/(\int s1(E)de)]$$

$$p3 = -\log [\int s3(E)\exp(\int (a1(x,y)\mu1(E)+a2(x,y)\mu2(E)+a3(x,y)\mu gd(E)+a4(x,y)\mu w(E))dl)dE/(\int s1(E)de)]$$

$$p4 = -\log [\int s4(E)\exp(\int (a1(x,y)\mu1(E)+a2(x,y)\mu2(E)+a3(x,y)\mu gd(E)+a4(x,y)\mu w(E))dl)dE/(\int s1(E)de)] \quad (2)$$

The projection data set (p1, p2, p3, p4) in an example may be acquired times through simulation and/or physical measurements. By using the combination of uniform materials with a length set of (L1, L2, L3, L4) of unity density of material-1, material-2, gadolinium, and tungsten, the integration value over a1, a2, a3 and a4 parameters in an example may be simplified to exemplary equations in (3), for example, neglecting the units:

$$L1 = \int a1(x,y)dl$$

$$L2 = \int a2(x,y)dl$$

$$L3 = \int a3(x,y)dl$$

$$L4 = \int a4(x,y)dl \quad (3)$$

The data set (p1, p2, p3, p4) in an example may be further processed such as for detector imperfection and beam hardening of water, for example, to yield new corrected projection data set (P1, P2, P3, P4). With sufficient material data coverage during the calibration process, the one to one relationship of the data set pairs of (P1, P2, P3, P4) and (L1, L2, L3, L4) in an example may be resolved. The inversion function fm( ) in an example may be captured using the data pairs, and expressed as in exemplary equation (4)

$$L1 = f1(P1,P2,P3,P4)$$

$$L2 = f2(P1,P2,P3,P4)$$

$$L3 = f3(P1,P2,P3,P4)$$

$$L4 = f4(P1,P2,P3,P4) \quad (4)$$

STEP 414 in an example provides calibration for obtaining the final inversion matrix fm( ) for example, through employment of a combination of simulation and measurements. During an exemplary calibration process, the measured data pairs of projections and material thicknesses may be used to adjust the functional form fm( ) captured in STEP 412. The functional form $f_m$( ) in an example converts measured projection data to material density integral, which may be employed to reconstruct material density images. The measured projections in an example may be employed to reconstruct x-ray attenuation images. An exemplary functional form fm( ) may be expressed in analytical format or as a lookup table. Exemplary logic flow 502 in an example employs the functional form fm( ) to obtain material density images.

In an exemplary CT scan with multiple kVps or multiple energy bins, the s projections $PP_s$ in an example may be measured, where s=N+2. These projections in an example may be associated with the same x-ray path and with different incident x-ray spectra. The determination of the $PP_s$ data set in an example substantially and/or completely defines integrated density of the two non K-edge materials and the N K-edge materials along the projection path where the projections are measured. FIG. 5 is a representation of an exemplary logic flow 502 for obtaining material specific projections and images. An exemplary physical scan of an object or a patient 22 may be performed in an exemplary decomposition of the N+2 materials for the two non k-edge materials and N k-edge materials. With the knowledge of the k-edge materials/contrast agents and the scanning parameters in an example functional forms $f_m$( ) with the same settings may be found from a pre-built database or built dynamically. STEP 504 in an example employs the K-edge knowledge of the N K-edge material contrast agents to select at least N+2 energy bins of the ED detector as the detector 20. In another example, STEP 504 in an example employs the K-edge knowledge of the N K-edge material contrast agents to select at least N+2 kVps scans. STEP 506 in an example perform at least N+2 measurements of the same projection path, with at least one scan that employs ED detectors as the detectors 20 and at least N+2 energy bins or with at least N+2 different kVp scans, as will be appreciated by those skilled in the art.

STEP 508 in an example employs the inversion matrix obtained during the calibration process with matching condition as the N+2 or more measurements to compute material specific projections. Logic flow 402 in an example generates the functional form fm( ). Logic flow 502 in an example employs the functional form fm( ) for image reconstruction. Through exemplary employment of the N+2 measured projection data acquired in STEP 506, STEP 508 in an example may compute integrated density of any materials among the N+2 materials, exemplary equation (5), $$LL1 = f1(PP1, PP2, PP3, PP4, \ldots PPs)$$

$$LL2 = f2(PP1, PP2, PP3, PP4, \ldots PPs)$$

$$LL3 = f3(PP1, PP2, PP3, PP4, \ldots PPs)$$

$$\ldots$$

$$LL1 = fs(PP1, PP2, PP3, PP4, \ldots PPs) \quad (5)$$

where PP1, PP2, . . . PPs in an example comprise the measured projections from a given x-ray path under s different spectra, s=N+2 f1( ), f2( ), . . . fs( ) in an example comprise the inversion functions, for example, captured through employment of the logic flow 402.

LL1, LL2, . . . LLs in an example comprise the density integrals defined by measured projection data from (PP1, PP2, . . . PPs) measurements.

Exemplary sufficient measurements from various x-ray paths may allow reconstruction of any of the N+2 material density images at STEP 510. STEP 510 in an example performs image reconstruction with material density integral projections to form material specific density images, for example, through employment of CT reconstruction techniques, as will be appreciated by those skilled in the art.

An exemplary implementation fits the inversion matrix fm( ) with data pairs to an Mth order of polynomials of N+2 projections at different incident spectra. An exemplary implementation employs M>1. An exemplary value of M set at a value from three (2) to six (6), inclusive, may serve to provide and/or obtain an acceptable, improved, enhanced, and/or good fit, for example, to reduce, minimize, and/or avoid inaccuracy of the fit carried into the final images as added noise and/or a shift in density value.

Figure 6:
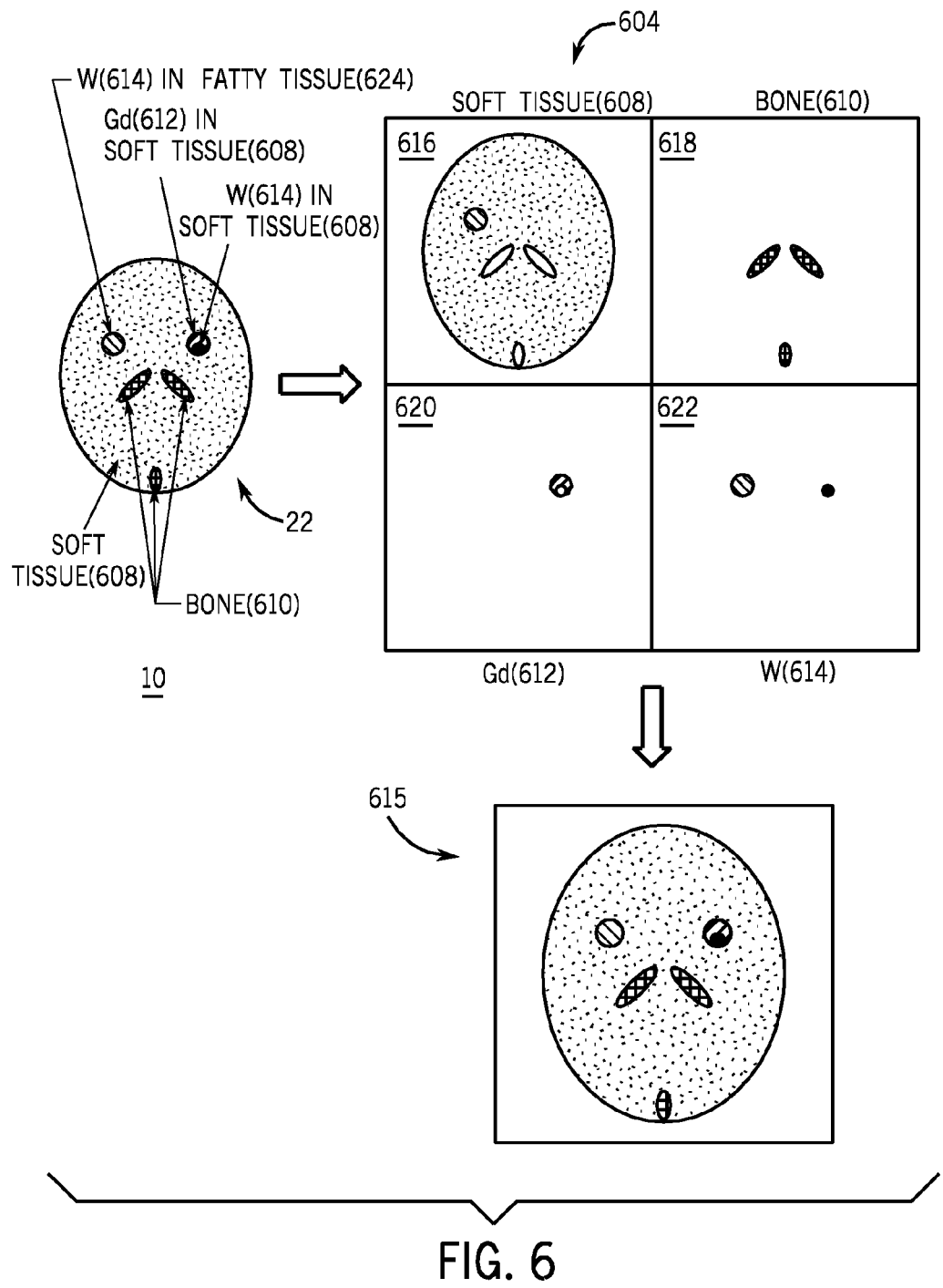
FIG. 6 is a representation of an exemplary phantom as a target object of an implementation of the system of FIG. 1, an exemplary decomposition of the phantom that employs a plurality of non K-edge materials and a plurality of K-edge materials and/or contrast agents, and a resulting image of the phantom.

FIG. 6 is a representation of an exemplary phantom as the target object 22, an exemplary decomposition 604 of the phantom that employs a plurality of non K-edge materials 608, 610 and a plurality of K-edge materials and/or contrast agents 612, 614, and a resulting image 615 of the phantom, for example, through employment of logic flows 402 and/or 502. An exemplary approach separates the phantom as the target object 22 into four materials 608, 610, 612, and 614 to obtain soft tissue image 616, bone image 618, gadolinium (Gd) image 620, and tungsten (W) image 622. The soft tissue and bone comprise exemplary non K-edge materials 608 and 610. The gadolinium (Gd) and tungsten (W) comprise K-edge materials 612, 614 as exemplary contrast agents.

FIG. 6 is a representation of an exemplary phantom as the target object 22, an exemplary decomposition 604 of the phantom that employs a plurality of non K-edge materials 608, 610 and a plurality of K-edge materials 612, 614 as contrast agents, and a resulting image 615 of the phantom, for example, through employment of logic flows 402 and/or 502. An exemplary approach separates the phantom as the target object 22 into four materials 608, 610, 612, and 614 to obtain soft tissue image 616, bone image 618, gadolinium (Gd) image 620, and tungsten (W) image 622. The soft tissue and bone comprise exemplary non K-edge materials 608 and 610. The gadolinium (Gd) and tungsten (W) comprise exemplary K-edge materials 612, 614 as exemplary contrast agents. In an exemplary implementation, the phantom as the target object 22 comprises 2 mg/cc gadolinium (Gd) as an exemplary K-edge material 612 in soft tissue 608, 2 mg/cc tungsten (W) as an exemplary K-edge material 614 in fatty tissue 624, 2.8 mg/cc tungsten (W) as an exemplary K-edge material 614 in soft tissue 608, and an exemplary phantom size of 18×22 cm.

Figure 7:
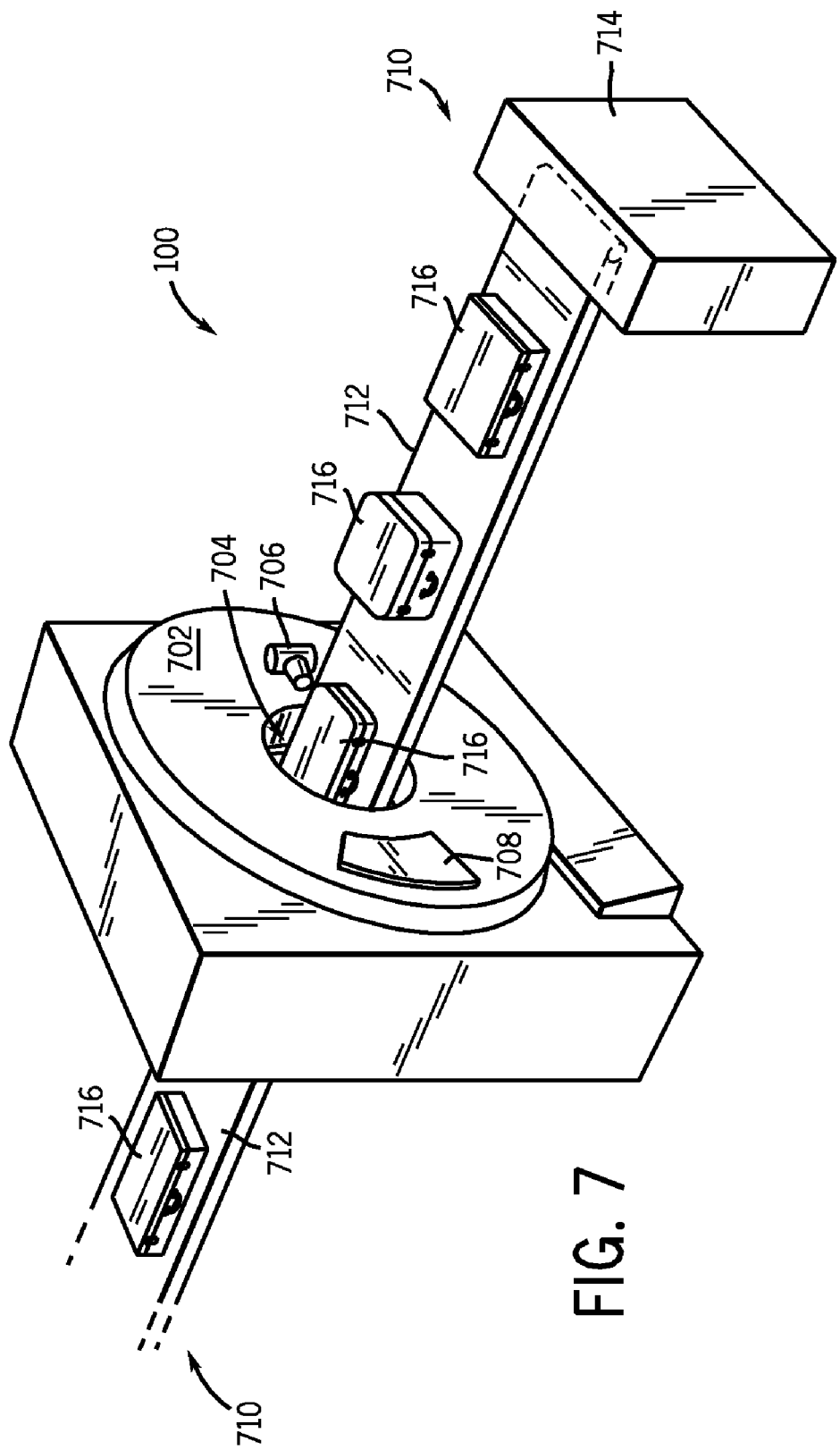
FIG. 7 is a pictorial view of a CT system for use with a non-invasive package inspection system.

Referring now to FIG. 7, package/baggage inspection system 100 includes a rotatable gantry 702 having an opening 704 therein through which packages or pieces of baggage may pass. The rotatable gantry 702 houses an x-ray and/or high frequency electromagnetic energy source 706 as well as a detector assembly 708 having scintillator arrays comprised of scintillator cells. A conveyor system 710 is also provided and includes a conveyor belt 712 supported by structure 714 to automatically and continuously pass packages or baggage pieces 716 through opening 704 to be scanned. Objects 716 are fed through opening 704 by conveyor belt 712, imaging data is then acquired, and the conveyor belt 712 removes the packages 716 from opening 704 in a controlled and continuous manner. As a result, postal inspectors, baggage handlers, and other security personnel may non-invasively inspect the contents of packages 716 for explosives, knives, guns, contraband, etc.

An exemplary implementation comprises a high frequency electromagnetic energy source 14, a detector 18, a data acquisition system (DAS) 32, and a computer 36. The high frequency electromagnetic energy source 14 emits a beam 16 of high frequency electromagnetic energy toward an object 22 to be imaged and be resolved by the system 10, 100. The detector 18 receives high frequency electromagnetic energy emitted by the high frequency electromagnetic energy source 14. The DAS 32 is operably connected to the detector 18. The computer 36 is operably connected to the DAS 32 and programmed to employ an inversion table or function to convert N+2 measured projections at different incident spectra into material specific integrals for N+2 materials that comprise two non K-edge basis materials 608, 610 and N K edge contrast agents 612, 614. N comprises an integer greater than or equal to 1.

The computer 36 operably connected to the DAS 32 is programmed to perform at least N+2 measurements or calibrations of the object 22 using different high frequency electromagnetic energy spectra. The computer 36 operably connected to the DAS 32 is programmed to match the at least N+2 measurements or calibrations of the object 22 and prior knowledge of the N K-edge contrast agents 612, 614 in an inversion matrix for individual material densities of the N+2 materials. An additional computer 36 is programmed to: perform at least N+2 measurements or calibrations of the object 22 using different high frequency electromagnetic energy spectra; and obtain the N+2 measured projections at the different incident spectra.

The computer 36 operably connected to the DAS 32 is programmed to solve an inversion matrix for individual material densities of the N+2 materials by inversion of data pairs representative of N+2 projections at the different incident spectra and input integrated densities of the N+2 materials. The high frequency electromagnetic energy source 14 comprises a high frequency polychromatic electromagnetic energy source 14 that emits a beam 16 of high frequency polychromatic electromagnetic energy toward the object 22 to be imaged. The detector 18 receives high frequency polychromatic electromagnetic energy emitted by the high frequency polychromatic electromagnetic energy source 14. N is greater than 1. The computer 36 operably connected to the DAS 32 is programmed to resolve simultaneously the N K-edge contrast agents 612, 614 in a single CT scan.

An exemplary approach calibrates a diagnostic imaging system 10, 100 through measurement of N+2 projections at different incident spectra of a substantially uniform mixture of a respective N+2 materials with known path integrated densities. The N+2 materials comprise two non K-edge basis materials 608, 610 and N K edge contrast agents 612, 614. N comprises an integer greater than or equal to 1.

The diagnostic imaging system 10, 100 is calibrated through measurement of the N+2 projections at the different incident spectra in a computer 36 simulation. The diagnostic imaging system 10, 100 is calibrated through measurement of the N+2 projections at the different incident spectra by the diagnostic imaging system 10, 100. The diagnostic imaging system 10, 100 is calibrated through employment of the N+2 projections at the different incident spectra to cover a possible path integrated density range for all the N+2 materials. The diagnostic imaging system 10, 100 is calibrated through employment of the N+2 projections at the different incident spectra to cover the possible path integrated density range for all the N+2 materials in small incremental steps.

Data pairs representative of the N+2 projections with the different incident spectra and input integrated densities of the N+2 materials at the different incident spectra are obtained. The data pairs are employed to generate an inversion table or function to convert the N+2 projections at the different incident spectra into material specific integrals for N+2 materials that comprise two non K-edge basis materials 608, 610 and N K edge contrast agents 612, 614. An inversion matrix for individual material densities of the N+2 materials is solved by inversion of the data pairs. The inversion matrix is fit with the data pairs to an Mth order of polynomials of the N+2 projections at the different incident spectra.

The object 22 is modeled with the two non K-edge basis materials 608, 610 plus the N K edge contrast agents 612, 614. Individual density projections for each of the plurality of K-edge contrast agents 612, 614 are obtained simultaneously through employment of an inversion matrix and N+2 projection measurements of a same projection path at N+2 incident energy spectra. Density of each of the plurality of K-edge contrast agents 612, 614 is analytically, non-iteratively resolved through reconstruction of the individual density projections. Each of the plurality of K-edge contrast agents 612, 614 is targeted to different tissues and/or organs in a single CT scan.

An exemplary implementation comprises a high frequency electromagnetic energy source 14, a detector 18, a data acquisition system (DAS) 32, and a computer 36. The high frequency electromagnetic energy source 14 emits a beam 16 of high frequency electromagnetic energy toward an object 22 to be imaged and be resolved by the system 10, 100. The object 22 is injectable with N K-edge contrast agents 612, 614. The detector 18 receives high frequency electromagnetic energy emitted by the high frequency electromagnetic energy source 14. The DAS 32 is operably connected to the detector 18. The computer 36 is operably connected to the DAS 32 and programmed to employ an inversion table or function to convert N+2 measured projections at different incident spectra into material specific integrals to resolve the object 22 with N+2 materials that comprise two non K-edge basis materials 608, 610 and the N K edge contrast agents 612, 614. N comprises an integer greater than 1.

An implementation of the system 10 and/or 100 in an example comprises a plurality of components such as one or more of electronic components, hardware components, and/or computer software components. A number of such components can be combined or divided in an implementation of the system 10 and/or 100. An exemplary component of an implementation of the system 10 and/or 100 employs and/or comprises a set and/or series of computer instructions written in or implemented with any of a number of programming languages, as will be appreciated by those skilled in the art. An exemplary technical effect is one or more exemplary and/or desirable functions, approaches, and/or procedures. An implementation of the system 10 and/or 100 in an example comprises any (e.g., horizontal, oblique, or vertical) orientation, with the description and figures herein illustrating an exemplary orientation of an implementation of the system 10 and/or 100, for explanatory purposes.

An implementation of the system 10 and/or the system 100 encompasses an article. The article comprises one or more computer-readable signal-bearing media. The article comprises means in the one or more media for one or more exemplary and/or desirable functions, approaches, and/or procedures.

An implementation of the system 10 and/or the system 100 in an example employs one or more computer readable signal bearing media. A computer-readable signal-bearing medium in an example stores software, firmware and/or assembly language for performing one or more portions of one or more implementations. An example of a computer-readable signal bearing medium for an implementation of the system 10 and/or the system 100 comprises the recordable data storage medium of the image reconstructor 34, and/or the mass storage device 38 of the computer 36. A computer-readable signal-bearing medium for an implementation of the system 10 and/or the system 100 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 100, for instance, one or more of a telephone network, a local area network ("LAN"), a wide area network ("WAN"), the Internet, and/or a wireless network.

The steps or operations described herein are examples. There may be variations to these steps or operations without departing from the spirit of the invention. For example, the steps may be performed in a differing order, or steps may be added, deleted, or modified The present invention has been described in terms of the preferred embodiment, and it is recognized that equivalents, alternatives, and modifications, aside from those expressly stated, are possible and within the scope of the appending claims.

What is claimed is:

1. A diagnostic imaging system, comprising:
a high frequency electromagnetic energy source that emits a beam of high frequency electromagnetic energy toward an object to be imaged and be resolved by the system;
a detector that receives high frequency electromagnetic energy emitted by the high frequency electromagnetic energy source;
a data acquisition system (DAS) operably connected to the detector; and
a computer operably connected to the DAS and programmed to:
calibrate the diagnostic imaging system to produce a non-linear inversion function; and
employ the non-linear inversion function to convert N+2 measured projections at different incident spectra into material specific integrals for N+2 materials that comprise two non K-edge basis materials and N K-edge contrast agents, wherein N comprises an integer greater than or equal to 1.

2. The diagnostic imaging system of claim 1 wherein the computer operably connected to the DAS is programmed to:
obtain at least N+2 calibration measurements of the object; and
access prior knowledge of the N K-edge contrast agents, wherein the calibration of the diagnostic imaging system is based on the at least N+2 calibration measurements and the prior knowledge of the N K-edge contrast agents.

3. The diagnostic imaging system of claim 1 further comprising:
an additional computer programmed to:
obtain the N+2 measured projections at the different incident spectra, wherein each of the N K-edge contrast agents comprises a K-edge at a respective K-edge energy, and wherein each of the respective K-edge energies is within a respective spectrum of the different incident spectra.

4. The diagnostic imaging system of claim 1 wherein the computer operably connected to the DAS is programmed to:
reconstruct, after a single scan, an image representative of each of the N K-edge contrast agents free of the non K-edge basis materials such that N images are reconstructed.

5. The diagnostic imaging system of claim 1 wherein the high frequency electromagnetic energy source comprises a high frequency polychromatic electromagnetic energy source that emits a beam of high frequency polychromatic electromagnetic energy toward the object to be imaged;
  wherein the detector receives high frequency polychromatic electromagnetic energy emitted by the high frequency polychromatic electromagnetic energy source.

6. The diagnostic imaging system of claim 5 wherein the computer operably connected to the DAS is further programmed to resolve simultaneously the N K-edge contrast agents in a single CT scan.

7. The diagnostic imaging system of claim 1 wherein N comprises an integer greater than 1.

8. A method, comprising:
  calibrating a diagnostic imaging system through measurement of N+2 calibration projections at different incident spectra of a substantially uniform mixture of a respective N+2 materials with known path integrated densities to determine a non-linear inversion matrix, wherein the N+2 materials comprise two non K-edge basis materials and N K-edge contrast agents, and wherein N comprises an integer greater than or equal to 1; and
  resolving the N+2 materials after a single CT scan via the non-linear inversion matrix such that a material density is resolved for each of the N+2 materials.

9. The method of claim 8, wherein calibrating a diagnostic imaging system comprises calibrating the diagnostic imaging system through measurement of the N+2 calibration projections at the different incident spectra in a computer simulation.

10. The method of claim 8, wherein N is an integer greater than 1.

11. The method of claim 8 wherein calibrating a diagnostic imaging system comprises calibrating the diagnostic imaging system through employment of the N+2 calibration projections at the different incident spectra to cover the possible path integrated density range for all the N+2 materials in small incremental steps.

12. The method of claim 8 wherein resolving the N+2 materials after a single CT scan comprises resolving each of the N k-edge contrast agents in a separate image free of the non K-edge basis materials such that N images are generated, wherein each image of the N images corresponds to one of the N K-edge contrast agents.

13. The method of claim 8 wherein calibrating a diagnostic imaging system comprises obtaining data pairs representative of the N+2 calibration projections with the different incident spectra and input integrated densities of the N+2 materials at the different incident spectra, and wherein resolving the N+2 materials comprises obtaining an additional N+2 projection of the N+2 materials.

14. The method of claim 13 further comprising fitting the non-linear inversion matrix with the data pairs to an Mth order of polynomials.

15. The method of claim 8 further comprising the step of obtaining simultaneously individual density projections for each of the N K-edge contrast agents through employment of the non-linear inversion matrix and N+2 additional projection measurements of a same projection path at N+2 incident energy spectra.

16. The method of claim 8 further comprising targeting each of the N K-edge contrast agents to at least one of different tissues and organs in a single CT scan, wherein N is an integer greater than 1.

17. A diagnostic imaging system, comprising:
  a high frequency electromagnetic energy source that emits a beam of high frequency electromagnetic energy toward an object to be imaged, wherein the object is injectable with N K-edge contrast agents;
  a detector that receives high frequency electromagnetic energy emitted by the high frequency electromagnetic energy source;
  a data acquisition system (DAS) operably connected to the detector; and
  a computer operably connected to the DAS and programmed to:
    calibrate the diagnostic imaging system to produce a non-linear inversion matrix;
    obtain N+2 projections at different incident spectra of N+2 materials from a single CT scan, the N+2 materials comprise two non K-edge basis materials and N K-edge contrast agents and each of the N K-edge contrast agents have a K-edge within one of the different incident spectra, and wherein N is an integer greater than or equal to one; and
    determine material densities from the N+2 projections for each of the N+2 materials based on the non-linear inversion matrix.

18. The method of claim 17 wherein N is an integer greater than 1.

19. The method of claim 17 wherein determination of the material densities of the N+2 projection comprises a reconstruction of N images after a single CT scan, wherein each of the N images corresponds to one of the N k-edge contrast agents and is free of the non K-edge basis materials.

* * * * *

UNITED STATES PATENT AND TRADEMARK OFFICE
CERTIFICATE OF CORRECTION

| | | |
|---|---|---|
| PATENT NO. | : 7,756,239 B2 | Page 1 of 1 |
| APPLICATION NO. | : 11/608162 | |
| DATED | : July 13, 2010 | |
| INVENTOR(S) | : Wu et al. | |

It is certified that error appears in the above-identified patent and that said Letters Patent is hereby corrected as shown below:

In Column 9, Line 16, delete "(E)de)]" and insert -- (E)dE)] --, therefor.

In Column 9, Line 18, delete "(E)de)]" and insert -- (E)dE)] --, therefor.

In Column 9, Line 21, delete "(E)de)]" and insert -- (E)dE)] --, therefor.

In Column 9, Line 24, delete "(E)de)]" and insert -- (E)dE)] --, therefor.

Signed and Sealed this

Twelfth Day of October, 2010

David J. Kappos
*Director of the United States Patent and Trademark Office*